United States Patent [19]

Okada

[11] Patent Number: 4,643,187

[45] Date of Patent: Feb. 17, 1987

[54] HIGH-FREQUENCY INCISING AND EXCISING INSTRUMENT

[75] Inventor: Tsutomu Okada, Hachioji, Japan

[73] Assignee: Olympus Optical Co., Ltd., Tokyo, Japan

[21] Appl. No.: 615,419

[22] Filed: May 30, 1984

[30] Foreign Application Priority Data

May 30, 1983 [JP] Japan ............................. 58-95530
Jul. 12, 1983 [JP] Japan ........................ 58-108851[U]
Jul. 20, 1983 [JP] Japan ............................ 58-133074

[51] Int. Cl.$^4$ ............................................. A61B 17/39
[52] U.S. Cl. ................................. 128/303.15; 128/320
[58] Field of Search ................. 128/303.1, 305, 751, 128/755, 756, 757, 320, 303.14, 303.15, 303.16, 304, 303.13, 303.17

[56] References Cited

U.S. PATENT DOCUMENTS 4,181,131  1/1980  Ogiu ............................. 128/303.15

FOREIGN PATENT DOCUMENTS

51-50377  12/1976  Japan .
56-104506  8/1981  Japan .

Primary Examiner—Michael H. Thaler
Attorney, Agent, or Firm—Armstrong, Nikaido, Marmelstein & Kubovcik

[57] ABSTRACT

A high-frequency incising and excising instrument for use in a body passage, the instrument having a wire loop for projection from the distal end of a tubular sheath and manipulated from the proximal end of the tube for hooking a phyma, polyp, growth, or the like, to be excised and for excising the phyma, polyp, growth, or the like, by applying high-frequency electric current to the wire loop. The instrument has a crescent wire loop formed by a wire bent at a bending portion. A slider, secured to the end portion of one side of the wire, is pressed in the advancing operation of the wire and moved sideways in the sheath to engage a guide on the inner wall of the sheath and to prevent rearward movement of the wire end so that pulling the bent side of the wire into the tubular sheath tightly binds the phyma, polyp, growth, or the like, to be incised and, upon completion of the incising, the wire can be drawn back into the tubular sheath.

7 Claims, 36 Drawing Figures

HIGH-FREQUENCY INCISING AND EXCISING INSTRUMENT

BACKGROUND OF THE INVENTION

This invention relates to an endoscope having a high-frequency incising and excising instrument by which polyps, tumors, growths, or the like, in and along internal passages of a human or animal body and accessible through a body opening can be incised and removed by passing a high-frequency current through a wire loop.

Endoscopes, in recent years, have become and continue to be more widely and extensively used in medical and industrial fields where areas not otherwise exposed or accessible can be viewed and procedures performed thereon. Two basic types of endoscopes are used, one having a hard or rigid distal end for insertion into the area to be viewed or where a procedure is to be performed and the other having a soft or flexible distal end. Where the distal end is soft or flexible, the soft or flexible end can be bent or deflected as it is inserted into the opening and passed throught the passage. In both instances, the endoscopes are designed so that the desired area or areas along the internal passage can be observed and dignosis made at the distal end from the remote or proximal end of the endoscope and so that, where required, treatment can be effected to the area at the distal end by means of instruments inserted through a channel in the endoscope and manipulated from the proximal end.

One medical procedure in which endoscopes, as described above, are commonly used is in the location, diagnosis and removal of phyma or polyps from the walls of the stomach. The stomach wall is examined from the distal end of the endoscope, the phyma or polyps are located and diagnosed and can then be excised by a high frequency incising and excising instrument inserted through the channel of a treatment instrument while being observed through the endoscope.

Figures 1A, 1B:
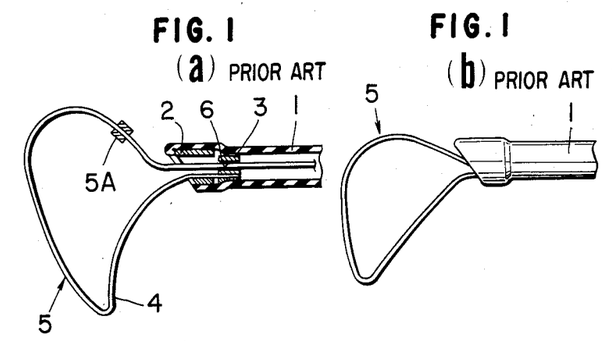
FIG. 1(a) is a longitudinal section view of a prior art instrument.
FIG. 1(b) is a side view of the instrument of FIG. 1(a), showing the wire loop in a first position in retraction.
Figure 1C:
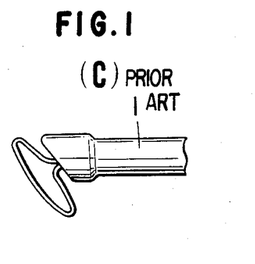
FIG. 1(c) is a side view, similar to FIG. 1(b) but showing the wire loop in a further position in retraction.

In Japanese Utility Model Publication No. 50377/76 there is disclosed an example of an incising and excising instrument having, as shown in FIG. 1(a) hereof, a ring 2 inside of a sheath at the distal end of a flexible tube 1. A freely advancing and retracting slider 3 is positioned inside of flexible tube 1, behind ring 2, and is fixed to the bent end portion 4 of wire loop 5. The opposite end of wire loop 5 extends through passage 6 in slider 3 and axially through tube to the proximal end, not shown, where the wire is fastened to a handle, loop, or other device by which the wire and wire loop 5 can be manipulated. By manipulating wire loop 5 from the opposite, or proximal end of flexible tube 1, loop 5 can be advanced from the sheath end of tube 1, the bent portion 4 of wire loop 5 can be hooked around the polyp to be incised and tightened, in the body cavity, around such polyp. By applying high frequency current to the wire loop, the polyp is burnt out. However, after the exercising of several polyps in this manner, carbides form on the wire loop, stick to the wire and the loop is deformed. As a result, high mechanical resistance to the advance and retraction of wire loop 5 through passage 6 in slider 3 is encountered. Thus, slider 3 is pulled toward the proximal or handle end of tube 1 before loop 5 is completely closed, resulting in the loop remaining open as shown in FIG. 1(b). When loop 5 is drawn further toward the proximal or handle end of tube 1 in an attempt to close the loop, the length of the loop, from the bent end portion 4 changes. As a result, a small loop is formed in a vertical direction to the longitudinal axis of the flexible tube 1, as shown in FIG. 1(c). The loop, even if further pulled, can not be closed. Thus, the instrument becomes useless. Under the worst conditions, the loop is frozen and can not be reopened. To overcome this problem, an annular stopper 5A, as shown in FIG. 1(a), is adhered to wire loop 5. When stopper 5A contacts slider 3, the slider is drawn into tube 1 and the bent portion 4 of wire loop 5 is drawn into the distal end of tube 1 after wire loop 5 is closed and exercising is completed.

Figure 2A:
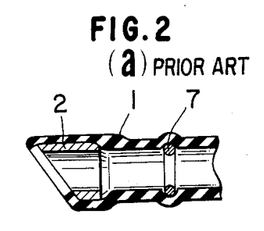
FIGS. 2(a), 2(b) and 2(c) are longitudinal section views of other prior art instruments.
Figure 2B:
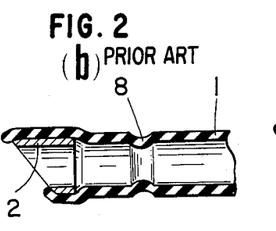
Figure 2C:
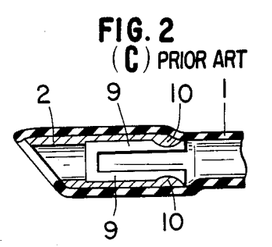

In Japanese Laid-Open Utility Model Application No. 104506/81 and as shown in FIG. 2 hereof, there is an improvement in the instrument of the afore described Utility Model Publication. In such improvement, a flexible C ring 7, FIG. 2(a), is mounted inside flexible sheath 1, a part of the sheath 1, as shown in FIG. 2(b), is formed to project inwardly as a convex portion, or, as shown in FIG. 2(c), a convex portion 10 is formed on lever 9 by extending the rear end side of the engagement ring 2. Where slider 5A, FIG. 1, is pushed forward through C ring 7, however, the C ring is pushed forward before slider 3 goes through C ring 7. This, of course, is not desirable. As to the convex portion 8 in FIG. 2(b), such convex portion tends to become flattened by the repeated movement of slider 3 through the convex portion. This, of course, is also not desirable. In the arrangement of FIG. 2(c), the engagement ring 2 forming the convex portion 10, when it contacts the inside of tube closely, prevents slider 3 from being pushed in and the flexibility of lever 9 of engagement ring 2 is lost. This, also, is not desirable.

BRIEF SUMMARY OF THE INVENTION

The instant invention provides a high-frequency incising and excising instrument capable of reliably opening and closing the wire loop when operation of the loop to opening and closing is otherwise increased by the sticking of carbides.

The instant invention further provides a high-frequency incising and excising instrument capable of incision and excision with safety and certainty.

Further, the instant invention provides such an incision and excising instrument of simple construction.

These and other features and advantages of the incision and excision instrument of the instant invention will be more fully understood from the description which follows.

DETAILED DESCRIPTION OF THE PREFERRED EMBODIMENTS

Figure 3:
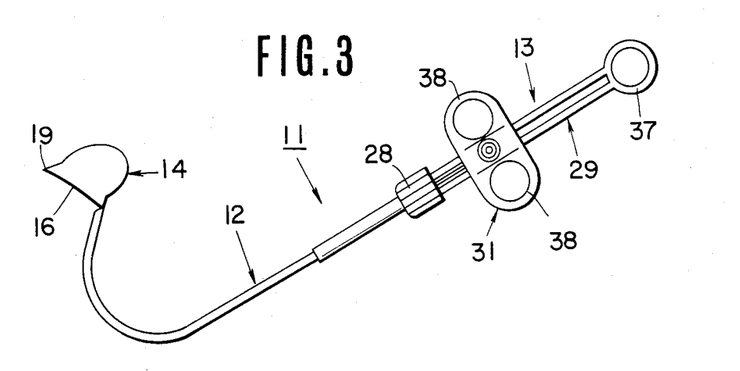
FIG. 3 is a perspective view of one embodiment of the incising and excising instrument of the instant invention.

As shown in FIG. 3, the high-frequency incising and excising instrument of the first embodiment of the instant invention, generally designated 11, includes a slender and flexible insertion, or distal end, portion, generally designated 12, for insertion through the channel of an endoscope, an operating portion, or proximal end, generally designated 13, to which the distal end portion 12 can be freely attached and detached, and a notched portion 14 to be projected from the forward, or distal end of the insertion portion 12.

Figure 4:
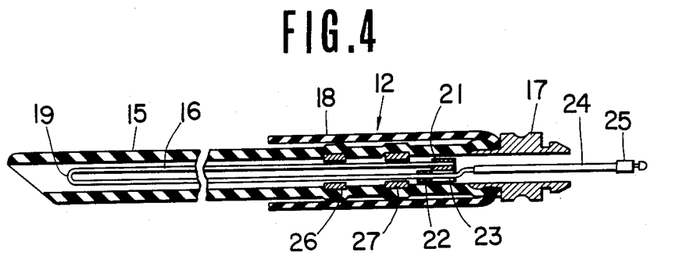
FIG. 4 is a longitudinal section view of the structure of the insertion portion, or distal end of the instrument of FIG. 3.

Flexible, tubular sheath 15, FIG. 4, is positioned in insertion portion 12. The front or forward end of sheath 15 is obliquely notched and open. Wire loop 16, for excision, is positioned in sheath 15 for projection from and retraction into sheath 15. At its rear end, sheath 15 is fitted and attached to one end of cap 17 and extends forwardly from cap 17 forming an outer circular sleeve spaced outwardly from sheath 15 to form a protective tube 18 around sheath 15 for preventing breakage and buckling of the sheath.

Figure 6:
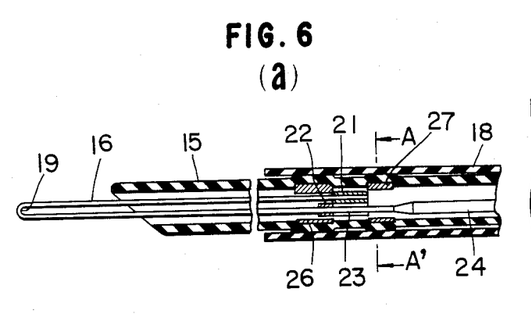
FIG. 6(a) is a longitudinal sectional view of the insertion or distal portion of the instrument of FIGS. 3 and 4 with wire projected.
FIG. 6(b) is an enlarged sectional view taken at A—A', FIG. 6(a).

Notched portion 14 includes a wire loop 16, having a bending portion 19, for retraction into and projection out of sheath 15. At one of its ends, wire loop 16 is secured to slider 21 which is freely extendable and retractable in sheath 15 for advancing and retracting wire loop 16. Annular stopper 22 is secured to the other end of wire loop 16 beyond bending portion 19. At the rear side of stopper 22, guide groove 23, as best shown in FIG. 6(b), is formed on slider 21. Operating pipe 24 is fixed to the end of wire loop. A fixing tool 25 is formed at the rear end of operating pipe 24.

Slider 21 has an outer diameter smaller than the inner diameter of sheath 15 and, thus, can be advanced and retracted freely in sheath 15. The outer diameter of slider 21 is greater than the inner diameter of the front engaging ring 26, secured to the inner wall of sheath 15. Thus, slider 21 is not movable forward from the fixed position of engaging ring 26 and the front engaging ring 26 forms a first engagement portion for controlling the forward movement of slider 21. The outer diameter of slider 21 is smaller than the inner diameter of the rear engagement ring 27 secured to the inner wall of sheath 15. When operating pipe 24 is not inserted through guide groove 23 of the slider, slider 21 can pass through rear engagement ring 27, FIG. 6(a). With operating pipe 24 inserted through guide groove 23, FIG. 7(a), slider 21 is pushed to the inner wall side of sheath 15 on side opposite to groove 23. Thus, slide 21 can not pass through rear engagement ring 27 and rear engagement functions as a second engagement portion to control the rearward movement of slider 21.

Figure 5:
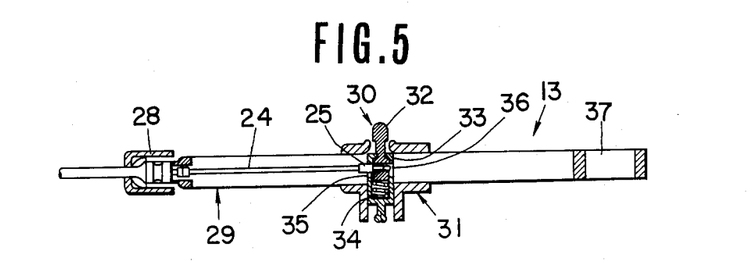
FIG. 5 is a longitudinal partial sectional view of the remote, or proximal end of the instrument of FIG. 3.

Operating portion 13, FIG. 5, includes an operation body 29, fixed to the rear end portion of the hand side of sheath 15 by a fixing member 28, and an operation slider 31 slidably fixed to the operation body 29 and forms a fixing core securing portion 30, making the rear end of loop wire 16 freely detachable and attachable with fixing core 25.

The fixing tool securing portion 30, FIG. 5, includes button 32 whose end portion projects upward from a hole formed in the center of operation slider 31, a frame 33 for containing the base side of button 32, and spring 34 which is contained in frame 33 and fuctions to project button 32 upwards. At the front side of frame 33 there is formed a hole 35 containing fixing core 25. On the base side of button 32, hole 36 communicates with hole 35 of frame 33. When button 32 is pressed down with the finger to insert fixing core 25 and the finger is released from button 32, fixing core 25 is held and attached with the force of spring 34.

Loop wire 16, to be connected to operating portion 13, is with high-frequency electric current from a high-frequency generating device via a cable, not shown, through fixing tool securing portion 30 and fixing core 25.

Ring-shaped finger rest 37 is formed at the rear or proximal end of operating body 29. Ring-shaped finger rests 38, 38, FIG. 3, are provided on operation slider 31. Operation slider 31 is moved back and forth, relative to operation body 29, by manipulating the finger tips on the finger rests 37, 38 and 38.

Operation slider 31 is pressed forward to project loop wire 16 from the end of sheath 15. Slider 21 passes through rear engagement ring 27 and contacts front engagement ring 26. Operating pipe 24, in contact with the side of guide groove 23 of slider 21, is pressed forward and loop wire 16, projecting from the front of sheath 15, on its side connected to operating pipe 24, is bent at the bending portion 19, FIG. 7(a), and forms a crescent shaped loop of a size sufficient for excision. Slider 21 is displaced longitudinally to engage front engaging ring 26 and is then displaced laterally by operating pipe 24 to be pressed against the inner wall of sheath 15. When operating pipe 24 is then pulled rearward, slider 21, pressed against inner wall of sheath 15 by pipe 24, is held in engagement with the end of rear engagement ring 27 to stop its rearward movement until operating pipe 24 passes through guide groove 23. Loop wire 16, projecting from sheath 15 is pulled back, or retracted into sheath 15 from its side having the greater bend, FIG. 9(a), and the loop is gradually tightened.

In the operation of the first embodiment, button 32 of the fixing tool securing portion 30, formed at operation slider 31, FIG. 5, is pressed to insert fixing core 25 at the rear end of operating pipe 24. Fixing core 25 is secured by then releasing button 32. Cap 17, at the rear of sheath 15, FIG. 4, is secured to the front end of operation body 29 by fixing member 28 and the instrument of the first embodiment is, thus, assembled.

The distal end of sheath 15 is inserted into the body cavity through the channel of the endoscope. The finger tips of the operator are placed in the finger rests 37, 38 and 38 of the operation body 29 and the operation slider 31. Slider 21 and loop wire 16 are advance in sheath 15. Thus, bending portion 19 of loop wire 16 is projected from the distal end of sheath 15. The front end of slider 21 contacts the rear side of front engagement ring 26 and slider 21 is stopped. As the advancement of loop wire 16 in sheath 15 continues, with slider 21 stopped, the cresent shaped loop in loop wire 16 is formed and enlarges at the bending portion 19, FIG. 7(a). Operation pipe 24 passes through guide groove 23 and slider 21 is pressed toward the inner wall of sheath 15 between front engagement ring 26 and rear engagement ring 27. The crescent shaped loop of projecting loop wire 16 is then hooked around the polyp, or the like, to be excised.

With loop wire 16 around the polyp, slider 31 is receded, or pulled back, by operating of finger rests 38, 38 of operation slider 31 toward finger rest 37 of operation body 29. Operating pipe 24 slides back through guide groove 23 and is pulled to the rear of sheath 15. Wire loop 16, at its bent portion 19 of greater bend, is decreased in loop size and is drawn back into sheath 15. Even if mechanical operation resistance is encountered because of carbides deposited on loop wire 16 during prior exercising, slider 21 is pressed to the inner wall surface of sheath 15 until operation pipe 24 is withdrawn through guide groove 23. Thus, the connection of slider 21 at rear engagement ring 27 is maintained until operation pipe 24 clears guide groove 23 and loop wire 16 tightly binds the neck of the polyp, or the like, in the loop of loop wire 16. High-frequency current is then applied to the wire and the polyp is burnt away and stopper 22 of loop wire 16 contacts the slider 21. The bending portion 19 of loop wire 16 is pulled back into sheath 15 as the polyp is burned away, completing the excision of the polyp in the body cavity.

In the embodiment thus described, there is provided guide groove 23, as a guide portion in the slider 21, which freely advances and retracts in the sheath 15 and forms an engagement means for preventing the rearward movement when pressed by the operation pipe 24 when the operation pipe 24 is in insertion contact with the guide groove 23 and, with the rear engagement ring 27, prevents the free end of the loop wire 16 from retracting until the loop in loop wire 16 is contracted. Thus, with a simple construction, the loop in loop wire 16 can be closed without failure and the excising can be carried out with certainty.

Figure 7:
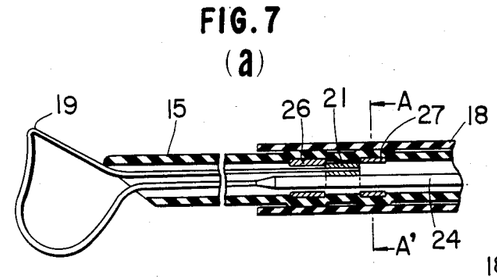
FIG. 7(a) is a longitudinal sectional view similar to FIG. 6(a) with the wire further projected.
FIG. 7(b) is an enlarged sectional view taken a A—A' FIG. 7(a).
Figure 8:
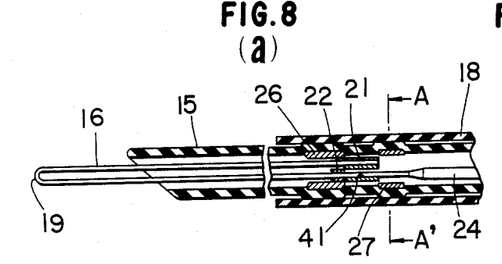
FIG. 8(a) is a view similar to FIG. 6(a) but of second embodiment of the invention.
FIG. 8(b) is an enlarged sectional view taken at A—A' FIG. 8(a).
Figure 9:
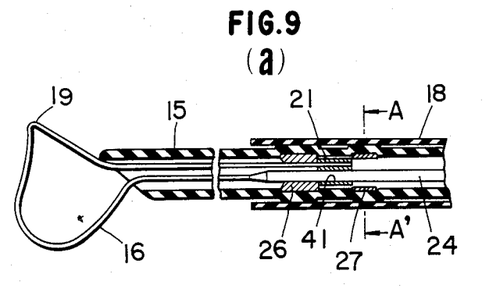
FIG. 9(a) is a view similar to FIG. 8(a) with the wire further projected.
FIG. 9(b) is an enlarged sectional view taken at A—A' FIG. 9(a).
Figure 10:
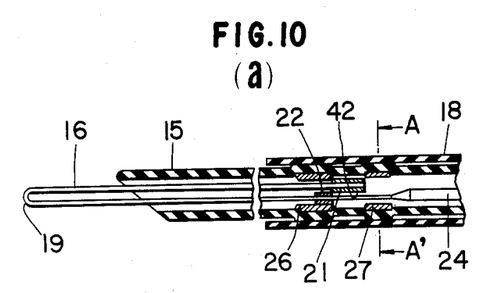
FIG. 10(a) is a view similar to FIGS. 6(a) and 8(a) but showing a third embodiment of the invention.
FIG. 10(b) is an enlarged sectional view taken at A—A' FIG. 10(a).
Figure 11:
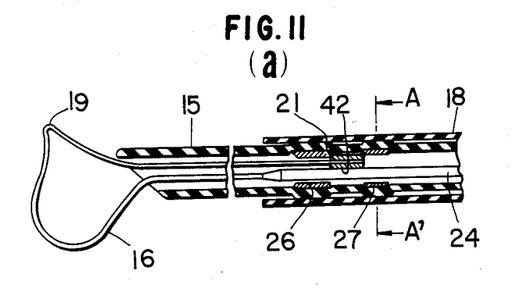
FIG. 11(a) is a view similar to FIG. 10(a) with the wire further projected. o
FIG. 11(b) is an enlarged sectional view taken at A—A' FIG. 11(a).

In the second embodiment of the invention shown in FIGS. 8(a), 8(b), 9(a) and 9(b) the guide groove 23 of the first embodiment, FIGS. 7(a) and 7(b), is replaced with a guide hole 41. As best shown in FIG. 8(a), guide hole 41 is formed in an eccentric manner in front engagement ring 26. When operating pipe 24 is inserted through guide hole 41, as shown in FIGS. 9(a) and 9(b), and pipe 24 and slider 21 are displaced in the longitudinal direction, slider 21 is pressed toward the inner wall of sheath 15 by the operation pipe 24 causing slider 21 to engage the forward end of rear engagement ring 27. Except for the replacement of the guide groove with a guide hole, the first and second embodiments work in the same manner.

In the third embodiment, FIGS. 10(a), 10(b), 11(a) and 11(b), a short crescent shaped slider 21 is employed. A cylinder having an outer diameter slightly smaller than the inner diameter of rear ring 27 is notched in a longitudinal direction to make the ring largely half-cylindrical. The half-cylinder 21 has a maximum length greater than the front engagement ring 26 to prevent half-cylinder 21 from moving forward past engagement ring 26. the operating pipe 24 is made to be inserted through the notched portion 42 as a guide portion. To insert operating pipe 24 through the notched portion 24, the half-cylindrical slider 21 is displaced in a longitudinal direction and pressed to the inner wall of sheath 15, thus giving a configuration wherein the slider 21 is pressed and displaced in a longitudinal direction relative to rear engagement ring 27, as shown in FIG. 11. The remainder of the instrument and the operation thereof are the same as in the first and second embodiments.

In the foregoing embodiments, the front engagement ring 26 and the rear engagement ring 27 are formed inside the protective tube 18. It is to be understood, however, that the invention is not limited to such particular location. Such front and rear engagement rings may be positioned near the end of sheath 15 or formed further toward the rear end of the sheath. The projection for engagement by the front engagement ring 26 or rear engagement ring 27 is not limited to being fixed inside sheath 15. A projection having substantially the same function can be formed by attaching a ring, or the like, around the outer circle of sheath 15 and inwardly projecting the inner circle of sheath 15 of the ring attached. Such configuration would be simpler than that of fixing the front engagement ring 26 or rear engagement ring 27 to the inside of sheath 15.

In the first and second embodiments, slider 21 may be formed of an elastic material, such as rubber, the guide groove 23 or guide hole 41 may be made of a smaller shape than the outer diameter of operating pipe 24 and the slider 21, upon insertion, can be displaced so as to be expanded in a longitudinal direction to be engaged with the projection of the rear engagement ring 27.

The present invention can be applied not only to excision but, also, to incision. The use of the invention is not limited to be inserted through the channel of a soft of a hard endoscope and sheath 15 is not limited to be formed as a flexible tube but also may be applied to a hard tube.

Figure 12:
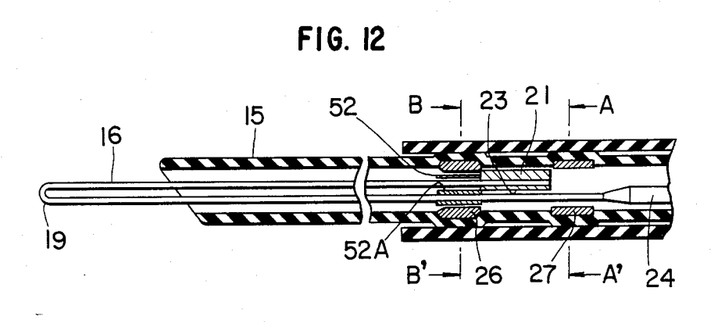
FIG. 12 is a view similar to FIGS. 6(a), 8(a) and 10(a) but showing a fourth embodiment of the invention.
Figure 13A:
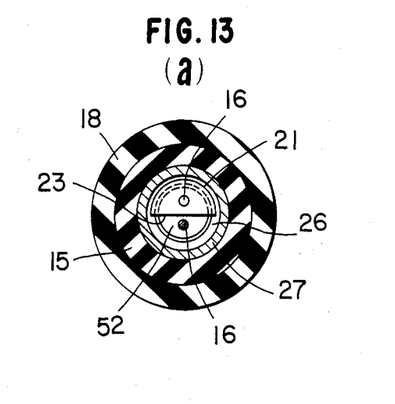
FIG. 13(a) is an enlarged sectional view taken at A—A' FIG. 12.
Figure 13B:
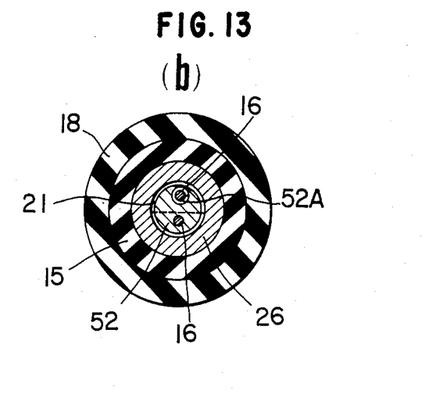
FIG. 13(b) is an enlarged sectional view taken at B—B' FIG. 12.

In the fourth embodiment, shown in FIGS. 12, 13(a) and 13(b), stopper 52 differs from stopper 22 in the third embodiment. As best shown in FIG. 12, stopper 52 is mounted in sheath 15 on the wire of wire loop 16 in front of operation pipe 24 and is fixed to the wire with an adhesive. Loop wire 16 bent, at bending portion 19, passes freely through guide port 52a in stopper 52. Slider 21 is fixed to the otherwise free end of loop wire 16 behind stopper 52. Stopper 52 has an outer diameter smaller than the inner diameter of front engagement ring 26 and, thus, passes easily therethrough. The stopper 52 also forms a guide port 52A through which the side of loop wire 16 fixed to the slider 21 can easily pass. The bending portion 19 of loop wire 16 retreats rearwardly and inwardly after excision and operating pipe 24 is retracted from the end of sheath 15 without failure.

At the time that the polyp, or the like, is burnt, slider 21 is pressed against the inner wall surface of the sheath 15 by operating pipe 24 and is in engagement with the rear engagement ring 27. Thus, when operating pipe 24 is pulled rearward to move stopper 52 rearward, loop wire 16 on the slider 21 side inserted through guide port 52A of stopper 52, is maintained at a prescribed interval with respect to the other side of loop wire 16 fixed to stopper 52. The guide port 52A functions to return loop wire 16, secured to the slider 21, to the central side and the engagement state with the rear engagement ring 27 is assuredly released after excision. Thus, slider 21, together with loop wire 16, moves rearward to cause the bending portion 19 to withdraw into the sheath 15.

Figure 14:
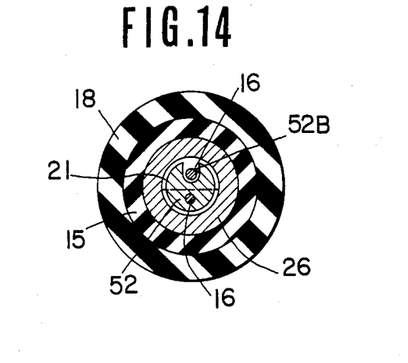
FIG. 14 is an enlarged sectional view of the stopper of the fifth embodiment of the invention.

In the fifth embodiment of the invention, shown in FIG. 14, there is formed, as the wire inserting guide portion of the stopper 52, an upper portion 52B, for receiving and passing the side of loop wire 16 secured to slider 21. The working effects of the fifth embodiment are the same as those described with respect to the fourth embodiment.

Figure 15:
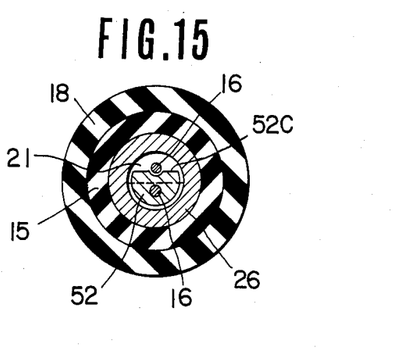
FIG. 15 is an enlarged sectional view of the stopper of the sixth embodiment of the invention.

In the sixth embodiment shown in FIG. 15, stopper 52 has a notched portion 52C which acts as a guide for the side of loop wire 16 secured to slider 21.

Figure 16:
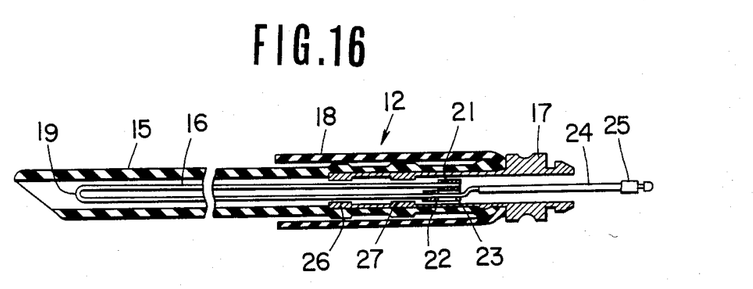
FIG. 16 is a view similar to FIG. 4 but showing the insertion portion of distal end of the seventh embodiment of the invention.

In the seventh embodiment shown in FIG. 16, the construction is similar to that of the first embodiment shown in FIG. 4. Here, however, the front engagement ring 26 and the rear engagement ring 27 are formed integrally with cap 17. Through the use of such cap and the integral arrangement, the engagement rings can be used for a prolonged period of time without change of positions despite repeated use. Otherwise, this embodiment has the same construction and operates in the same manner as the first embodiment.

Figure 17:
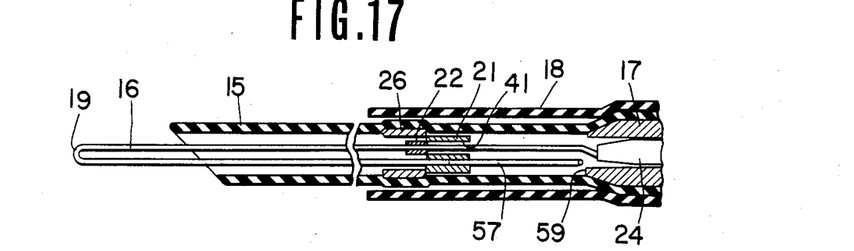
FIG. 17 is a view similar to FIGS. 6(A), 8(a), 10(A) and 12 but showing the eighth embodiment of the invention.
Figure 18:
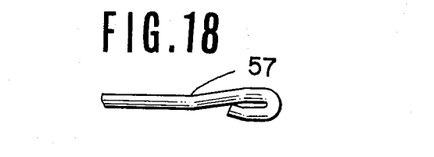
FIG. 18 is a front enlarged view of the reverse stop member of FIG. 17.
Figure 19:
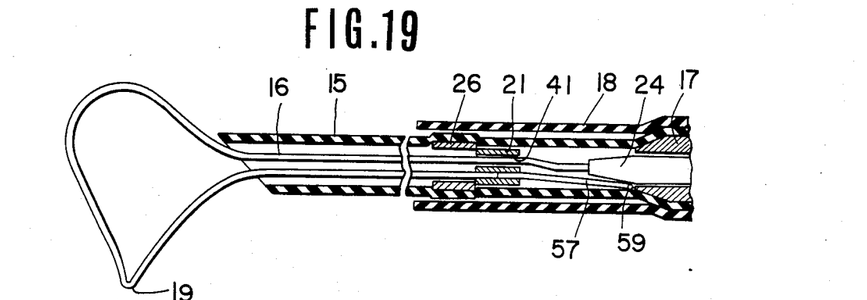
FIG. 19 is a view similar to FIG. 17 but showing the wire projected with the wire loop formed.

The eighth embodiment, shown in FIGS. 17 to 19, has a construction similar to the second embodiment in FIG. 8, with the rear engagement ring 27 of FIG. 8 replaced with a sideward moving portion 57. An engagement portion 59, at the front end of cap 17, serves as a rear stop for the portion 57 for limiting rearward movement of the free side of loop wire 16. Portion 57, acting as a reverse stop, is formed, for example, by a relatively hard single-wired member secured to the end of loop wire 16 in slider 21 fixed to the port inner wall. The outer end of reverse stop portion 57, extended to the hand side, is bent as, for example, shown in FIG. 18. When operating pipe 24 is moved forward and when, as shown in FIG. 17, bending portion 19 of loop wire 16 is projected from the front or distal end of sheath 15, causing slider 21 to contact front engagement ring 26, the rear end of reverse stop portion 57 is set to have a length equivalent to the length of its obtaining a position immediately before the position adjacent to the engagement portion 59. Thus, when the operating pipe 24 is pressed forward, the rear end of reverse stop portion 57, coming into contact with the taper portion at its front end, moves sidewards, is pressed to the inner wall surface of sheath 15 and is maintained in an engagement state in which its rearward movement is hindered by engagement portion 59. At this time, the portion of loop wire 16 projecting from sheath 15 can be formed into an almost crescent loop bent at the bending portion 19.

The crescent loop, projected from sheath 15 in the eighth embodiment of the invention, can be hooked on a phyma like polyp, of the like, when slider 31 is retracted, the operating pipe 24 is withdrawn to the rear of sheath 15 with its side portion is in contact with reverse stop portion 57. At the same time, the side of loop wire 16, greatly bent at the bending portion 19, has a low bending degree to close the loop. Even if operation resistance, due to carbides produced in prior excision have increased and the wire loop is sticky, the slider 21 is maintained in an engagement state until the operation pipe 24 moves more rearward than the rear end of reverse stop portion 57 and portion 57 is released from pressing the inner wall of sheath 15, since the rearward movement of reverse stop portion 57 is stopped by engagement portion 59. Accordingly, during the time that the operating pipe 24 is moved to the rear of reverse stop portion 57, the neck portion of the polyp is tightly bound by loop wire 16 since the side of loop wire 16 greatly bent in a crescent loop comes to have a low bending degree, in combination with the rearward movement of operating pipe 24. When a high-frequency electric current is applied to loop wire 16 in this state and the operation slider 31 is retracted, the polyp is burnt and the stopper 22 secured to loop wire 16 contacts slider 21. At the same time, operating pipe 24 is moved more rearward than reverse stop portion 57 and reverse stop portion 57 is released from being pressed to the inner wall of sheath 15 and moves to the more central side than the inner diameter of engagement portion 59 at the front end of cap 17. When the operating slide is further retracted, slider 21 retracts in an engagement state of contacting stopper 22. The bending portion 19 of loop wire 16 is withdrawn into sheath 15 in a state where the end projected from sheath 15 of loop wire 16 is the bending portion 19, completing the incision of the polyp in the body cavity. The reverse stop portion 57 in slider 21 freely advances and retracts inside sheath 15. An engagement means is formed by which the reverse stop portion 57 is connected to engagement portion 59 by displacing the reverse stop portion in a longitudinal direction when the operating pipe 24 is inserted while contacting the reverse stop member 57. Thus, with a simple construction, the loop can be closed without failure and only the desired position can be excited with certainty. The opening and closing of the loop wire 16 can be done without failure, safe and reliably.

Figure 20:
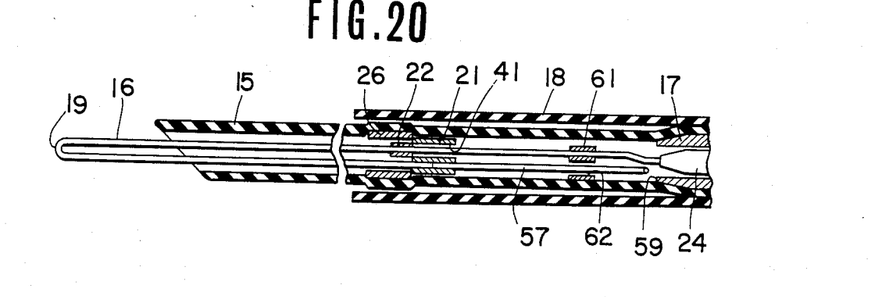
FIG. 20 is a view similar to FIGS. 6(a), 8(a), 10(a), 12 and 17 but showing the ninth embodiment of the invention.
Figure 21:
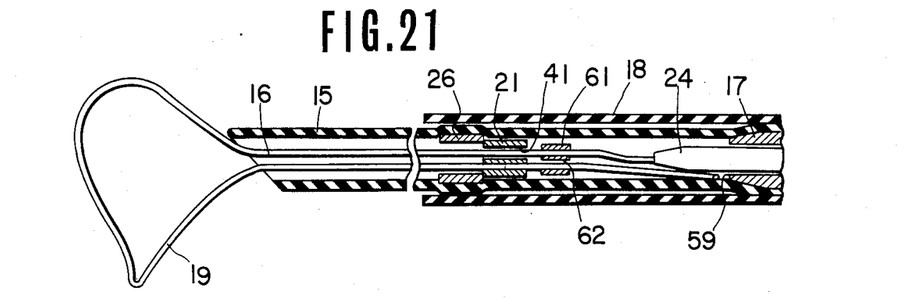
FIG. 21 is a view similar to FIG. 20 with the wire projected and forming a loop.

In the ninth embodiment shown in FIGS. 20 and 21, binding body 61 is secured to loop wire 16 adjacent to port 62 for allowing reverse stop portion 57 to pass therethrough. The reverse stop portion 57 is maintained integrally with loop wire 16 by the binding body 61. Thus, the deformation of reverse stop portion 57 is prevented.

Figure 22:
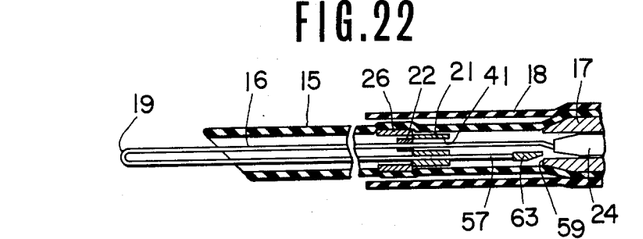
FIG. 22 is a view similar to FIGS. 6(a), 8(a), 10(a), 12, 17 and 20 but showing the tenth embodiment of the invention.
Figure 23:
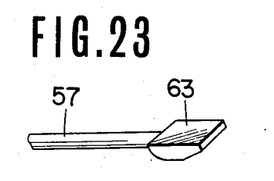
FIG. 23 is a perspective view showing the reverse stop member of the embodiment of FIG. 22 enlarged.

In the tenth embodiment shown in FIG. 22, the rear end of reverse stop member is not in the bent shape, as shown in the embodiment of FIG. 18, but is a tip 63 in the shape shown in FIG. 23 and is securely hooked by the engagement portion 59 at the front end of cap 17.

Figure 24:
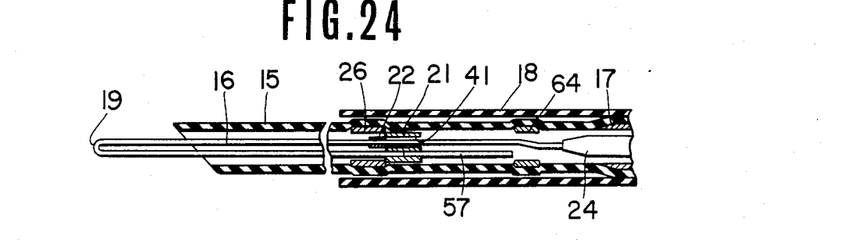
FIG. 24 is a view similar to FIGS. 6(a), 8(a), 10(a), 12, 17, 20 and 22 but showing the eleventh embodiment of the invention.
Figure 25:
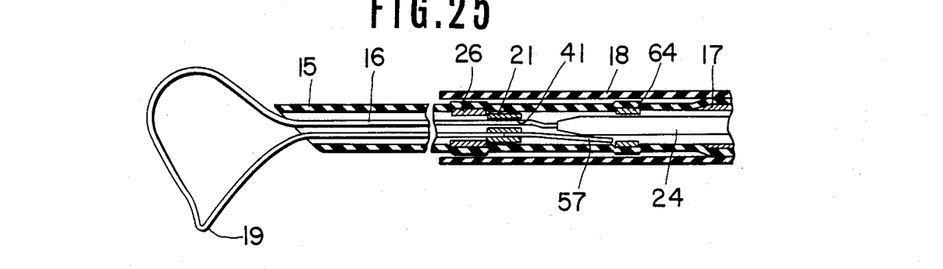
FIG. 25 is a view similar to FIG. 24 with the wire projected and forming a loop.

In the eleventh embodiment shown in FIGS. 24 and 25, engagement ring 64 is secured to the inner wall of sheath 15. Reverse stop portion 57, when deflected downward by contact with operating pipe 24 abuts ring 64, as best shown in FIG. 25. Except for such contact, the operation of this embodiment is substantially the same as in the eighth embodiment described above.

The guides, guide stops, engagement rings and the like, in the instant invention can obviously be of a variety of forms and shapes and in a variety of locations both within and outside of the sheath.

The terms and expressions which have been employed in the foregoing description are used as terms of description and not of limitation, and there is no intention, in the use of such terms and expressions, of excluding any equivalents of the features shown and described, or portions thereof, but it is recognized that various modifications are possible within the scope of the invention claimed.

I claim:

1. A high-frequency incising and excising instrument in which excision is made by applying a high-frequency current to a crescent loop in a wire extended from the front end of a tubular sheath and bent into a crescent loop and hooked around the portion to be excised and tightened therearound, said instrument being characterized by having a slider having a diameter larger than the diameter of the wire and smaller than the inside diameter of said sheath and fixed to the end of the bent wire at one side of said loop, said slider having a passage for free advance and retraction of said wire at the other side of said loop through said slider and being free to be advanced and retracted in said sheath; a wire movement operating pipe connected to said wire at said other side of said loop and movable in said sheath and having a diameter at the connection to said wire larger than the diameter of said wire; a stopper secured to said wire at the wire loop side of said slider for engaging said slider and retracting said slider and said wire loop into said sheath when said wire movement operating pipe is retracted for retracting said slider and said wire loop; a first engagement member having an inside diameter smaller than the outside diameter of said slider attached to said sheath for engaging said slider and for holding said slider and said one side of said wire loop fixed to said slider as said wire movement operating pipe advances said wire and bends said bent end of said wire into said crescent loop; said operating pipe and said first engagement member including means for moving said slider laterally in said sheath for engaging the forward end of said slider with said first engagement member and pressing said slider into engagement with a rearward end of said first engagement member as said operating pipe is advanced; and a second engagement member having an inside diameter larger than the outside diameter of said slide attached to said tubular sheath rearward from said front end of said sheath and from said first engagement member, said means for moving said slider laterally in said sheath including means for engaging the rear end of said slider with the forward end of said second engagement member and holding said slider between said first and second engagement members until said operating pipe is retracted and said moving means for moving said slider laterally in said sheath is released.

2. The high-frequency incising and excising instrument of claim 1 wherein said slider has a guide portion said passage for advance and retraction of said wire for engaging said larger diameter operating pipe connection as said connection is advanced and retracted through said slide for moving and holding said slider engaged between said first and second engagement members.

3. The high-frequency incising and excising instrument of claim 2 wherein the second engagement member is formed integrally with a cap at the rear end of the sheath.

4. The high-frequency incising and excising instrument of claim 1 wherein said slider further includes a slender member projected rearward from the slider.

5. The high-frequency incising and excising instrument of claim 4 wherein the second engagement member is a circular member attached to the inner wall of said sheath.

6. The high-frequency incising and excising instrument of claim 4 wherein the second engagement member has a cap formed at the rear end of the sheath, the front end of said cap having a stopper portion having a smaller diameter than the inner diameter of the sheath.

7. The high-frequency incising and excising instrument of claim 2 or 4 wherein the first and second engagement members are formed integrally with a cap at the rear end of the sheath.

* * * * *